United States Patent [19]

Pekrul et al.

[11] 4,060,716

[45] Nov. 29, 1977

[54] METHOD AND APPARATUS FOR AUTOMATIC ABNORMAL EVENTS MONITOR IN OPERATING PLANTS

[75] Inventors: Paul J. Pekrul, Canoga Park; Alfred W. Thiele, Woodland Hills, both of Calif.

[73] Assignee: Rockwell International Corporation, El Segundo, Calif.

[21] Appl. No.: 578,558

[22] Filed: May 19, 1975

[51] Int. Cl.$^2$ .............................................. G21C 17/00
[52] U.S. Cl. ..................................... 364/576; 176/19 J
[58] Field of Search ............................. 235/151.3, 151; 176/19 R, 20; 73/67; 340/172.5, 261; 445/1

[56] References Cited

U.S. PATENT DOCUMENTS

| | | | |
|---|---|---|---|
| 3,324,458 | 6/1967 | MacArthur | 340/172.5 |
| 3,400,374 | 9/1968 | Schumann | 235/151.1 X |
| 3,753,852 | 8/1973 | Scott et al. | 176/19 R |
| 3,778,347 | 12/1973 | Giras et al. | 176/20 X |
| 3,809,870 | 5/1974 | Auble et al | 235/151.3 |
| 3,860,480 | 1/1975 | Carteus et al. | 176/19 R |

Primary Examiner—Edward J. Wise
Attorney, Agent, or Firm—L. Lee Humphries; Henry Kolin; Clark E. DeLarvin

[57] ABSTRACT

An apparatus and method for automatically monitoring dynamic signals, such as from vibration sensors, in an operating industrial or other plant to identify abnormal events, draw conclusions as to their severity, and indicate action to be taken, utilizing a computer to control the scanning of one or two sensor channels at a time through a matrix of analog switches, and to process one or two channel signals through a signal processor for power spectral density (PSD) analysis (two channel signals for cross PSD analysis). The computer compares spectra with predetermined sets of frequency dependent limits and indicates the abnormal condition of apparatus in the plant associated with the spectra as a function of which set of limits is exceeded. The computer also indicates from a stored table the action to be taken for the abnormal condition found.

20 Claims, 6 Drawing Figures

METHOD AND APPARATUS FOR AUTOMATIC ABNORMAL EVENTS MONITOR IN OPERATING PLANTS

BACKGROUND OF THE INVENTION

This invention relates to abnormal event monitors, and more particularly to dynamic signal monitors for parts of operating plants that are not readily accessible for inspection.

Some plants are designed to operate for extended periods, such as nuclear power plants. Inspection is virtually impossible in many of these plants without shutting down. Yet it would be desirable to continually seek out potential problems, analyze them as to severity and indicate what action should be taken.

Loose parts in a nuclear power plant can cause a variety of problems. In view of this, loose parts monitoring of nuclear power plants has become common practice. A typical loose part monitor is disclosed in U.S. Pat. No. 3,860,481. Monitoring is accomplished on-line by picking up impact energy of a loose part by a suitable sensor attached to it, and detecting the energy at the resonant frequency of the loose part. The output of the sensor is analyzed as to the rate and the energy with which impact of the loose part occurs. However, this only indicates that a part being monitored has become loose, and does not provide information as to other conditions that may indicate a malfunction, or that would indicate a potential malfunction. For free and loose part detection, still other techniques have been developed as disclosed in U.S. Pat. Nos. 3,681,976 and 3,534,589.

Nondestructive testing of pressure vessels, and the like, have been devised based on monitoring and analyzing stress waves as disclosed in U.S. Pat. No. 3,545,262, and based on ultrasonic pulsing techniques as disclosed in U.S. Pat. No. 3,857,052. Stress wave analysis is not, however, suitable for on-line monitoring, and ultrasonic pulsing techniques are limited to applications where an ultrasonic transducer can be positioned or caused to be positioned from a remote console.

What is required is a system for continuously monitoring a plant on-line for anomalous behavior in which the monitor becomes part of the plant instrumentation and requires no operator action unless and anomalous condition is detected. Such a monitoring system can decrease operating costs by preventive maintenance techniques.

In any particular system there will be a number of key parameters which can be easily monitored, such as temperature and pressure. However, it would not be sufficient to monitor these parameters as they would, in general, indicate only when an alarm condition is reached, and provide no opportunity to diagnose potential malfunction due to impending failure of some part, such as a pump or motor.

It has been recognized that operating machinery will have characteristic vibrations which will vary if the machinery is not operating properly or if some part begins to deteriorate. See for example U.S. Pat. Nos. 3,641,550 and 3,758,758. For effective monitoring, the vibration signals of interest must be identifiable above the background noise, which means that a baseline (background) record of the sensor signal must be made to serve as a reference for comparison purposes later. Both the linear vibration and nonlinear loose parts signals must be detected and identified above the background noise. For cost effectiveness, the sensors employed should be passive, rather than active as in the ultrasonic system disclosed in U.S. Pat. No. 3,753,852 for monitoring vibrations in a nuclear reactor. However, the use of passive sensors makes the background noise problem more severe.

Monitoring the vibration energy of a cutting tool and comparing it with a reference has been recognized as an effective way of determining wear for the purpose of determining the optimum time to change the tool. See for example U.S. Pat. Nos. 3,694,637 and 3,841,149. But monitoring a single tool is not the same problem as monitoring an operating plant. Plants usually have complex vibrational patterns due to various components operating independently. To complicate things even more, some components operate independently and unsynchronized, and some even operate intermittently.

The development of programmed digital computers has made monitoring systems for complex operating plants feasible, as disclosed in U.S. Pat. No. 3,142,820. In that monitoring system, variables of the plant are monitored for comparison with operating limits. That will permit control of the plant, as by computing new set points for factors controlling the variable, and will, of course, permit alarm conditions to be detected and announced. The problem is that a failing component may, in the process, be overloaded to cause a complete break down. It would be desirable to monitor the vibrations of key components and points in the plant, not for control as disclosed in U.S. Pat. No. 3,710,082 in a vibration testing environment, but to find potential malfunctions, draw some conclusions as to their severity, and then indicate to the operator what action he should take for preventive maintenance.

OBJECTS AND SUMMARY OF THE INVENTION

An object of this invention is to provide for automatically diagnosing potential malfunctions in an operating plant and indicating any action to be taken for preventive maintenance.

Another object of the invention is to monitor dynamic signals at selected points of an operating plant and perform power spectral density (PSD) analysis on the signal at selected points and cross PSD analysis between selected points to diagnose potential malfunctions and indicate preventive maintenance action, if any, to be taken.

Still another object is to compare PSD data from selected points with frequency dependent limits so as to detect changes from baseline conditions.

Yet another object is to store PSD data in a historical file for comparison with current data to determine trends and rate of change in equipment.

In accordance with the present invention, monitoring of dynamic signals, particularly time-dependent fluctuating signals such as from vibration- and pressure-monitoring sensors at selected points on an operating plant is maintained for detecting potential malfunctions, such as fatigue-type of mechanical failure, drawing conclusions as to their severity, and indicating to operators what action should be taken by: sensing physical conditions at predetermined points monitored by sensors; employing a plurality of analog signal processing channels to detect subaudio frequency condition and low frequency condition signals in the range from about 0.01Hz to 1kHz, and high frequency noise signals above 1kHz to about 100kHz; placing all of the channels under computer control selection for digital power spectral density (PSD) analysis, including cross PSD analysis of selected channels; employing the computer to compare PSD data with predetermined frequency dependent limits; and interpreting the result of these comparisons into diagnostic conditions and indicating appropriate operator action from a prerecorded message library. In addition to this, a historical PSD data file is maintained for comparison of PSD data with baseline conditions prerecorded in digital form from initial PSD calculations, and with subsequent PSD calculations in order to determine trends and the rate of change in failing equipment.

DESCRIPTION OF THE PREFERRED EMBODIMENTS

Figure 1:
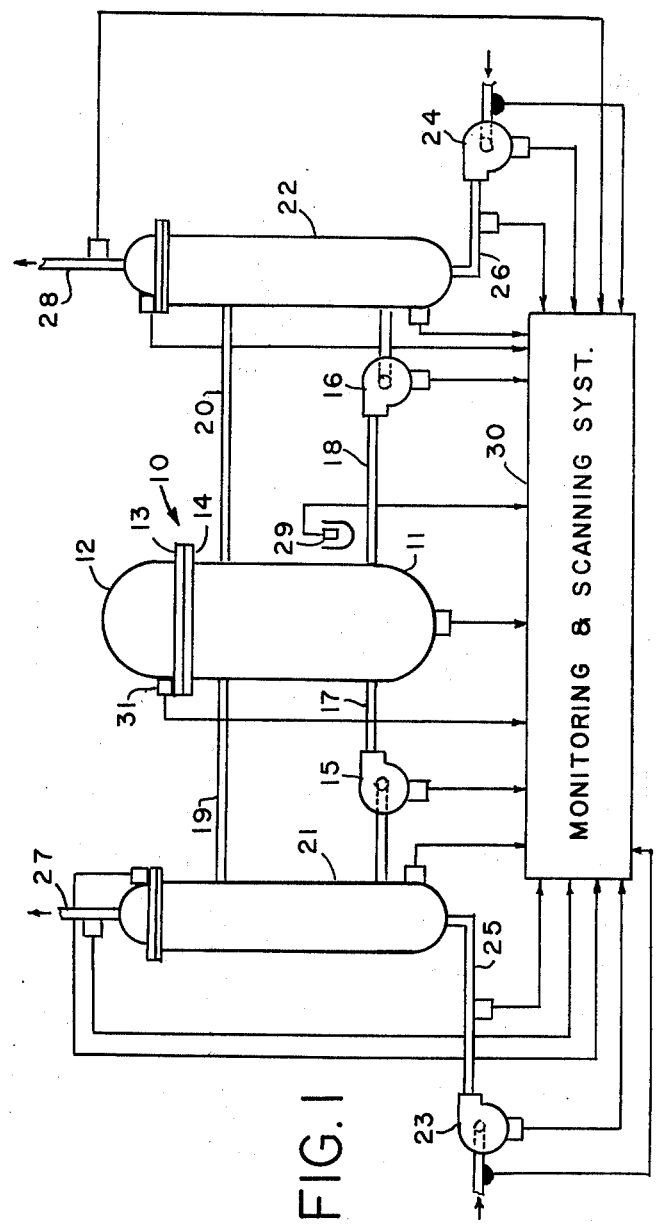
FIG. 1 is a schematic diagram of an exemplary operating plant illustrating exemplary locations of physical condition sensors and an automatic monitoring and scanning system incorporating the present invention.

FIG. 1 illustrates a typical application of the present invention to a nuclear reactor 10 for a steam driven electric generator (not shown). The reactor is comprised of a pressurized lower vessel 11 sealed by an upper vessel 12, through flanges 13 and 14. The reactor includes a nuclear core which generates substantial amounts of controlled heat. Pumps 15 and 16 circulate a coolant through the reactor. The coolant enters through inlets 17 and 18, and exits through outlets 19 and 20. The heated coolant is then circulated through steam generators 21 and 22 which are essentially only heat exchange units. Pumps 23 and 24 provide water under pressure through inlets 25 and 26 into the sealed chambers of the steam generator through which the coolant flows in spaced apart tubes. The chambers are comprised of upper and lower vessels held together by bolts through flanges in a manner similar to the reactor. Steam produced by the generators passes through outlets 27 and 28 to a turbine which drives a rotor for the production of electricity.

Abnormal vibrations can occur in the reactor due to some internal failure. For early detection of such a failure, a neutron flux sensor 29 monitors the coolant and generates an analog signal sent to a monitoring and scanning system 30. Once detected, the plant must be shut down until the problem is corrected. It can be appreciated that if the impending failure could be anticipated in sufficient time, it would be possible to avoid it through routine preventive maintenance. To accomplish that, a vibration sensor 31, such as a triple-axis piezo-electric accelerometer, is attached to the flange 13. The composite signal (vector sum of vibration components) generated by the sensor 31 is sent to the monitoring and scanning system. (Preamplifiers are assumed to be located at the site of the sensors to transmit analog signals over cables typically 500 feet long). Vibration sensors are similarly attached to the pumps and steam generators, and coupled to the monitoring and scanning system through cables. Each sensor may be a triple-axis sensor, as the sensor 31, or all (including the sensor 31) may consist of a single axis sensor. In the event separate vibration monitoring is desired at any one point in three orthogonal axes, three sensors may be provided, each coupled by a separate cable as a distinct input to the monitoring and scanning system.

These sensors could be used on any other type of plant as well as a nuclear plant. There is nothing unique about a nuclear plant with respect to the manner in which vibration signals from the sensors are used to find potential malfunctions, draw some conclusions as to their severity and then indicate to operators what preventive action he might take. The signals may also be used by monitoring and scanning systems to detect any unusual event, such as impact of a loose part, and to energize an alarm to call the event to the attention of the plant operators. As will be described more fully with reference to FIG. 2, the sensor signals are recorded on FM tape recorders 57 for record keeping and processed through a real-time signal processor for power spectral density analysis. Alarms insure instant operator attention to a potential damage or failure while spectral analysis of vibrations provide a highly refined, detailed record of plant dynamic characteristics through which identification and evaluation of potential failure mechanisms is made possible over a wide frequency range. PSD plots taken at regular intervals are examined by the monitoring and scanning system for limits, changes and trends as the basis for failure prevention through timely indication of necessary preventive maintenance.

Identification and location of excessive vibration requires characterization of the sensor signal for an observed condition. As will be described more fully hereinafter with reference to FIGS. 4 and 5, frequency range and amplitude limits of a PSD are predetermined and examined for a particular channel to determine whether it is exhibiting any anomaly. This requires the vibration signals to be identifiable above background noise. To accomplish that, a baseline PSD is recorded for each channel, or pairs of channels to be cross correlated to serve as a reference. Both anomalous conditions and impacts from loose parts must be detected and identified above the background noise.

Figure 2:
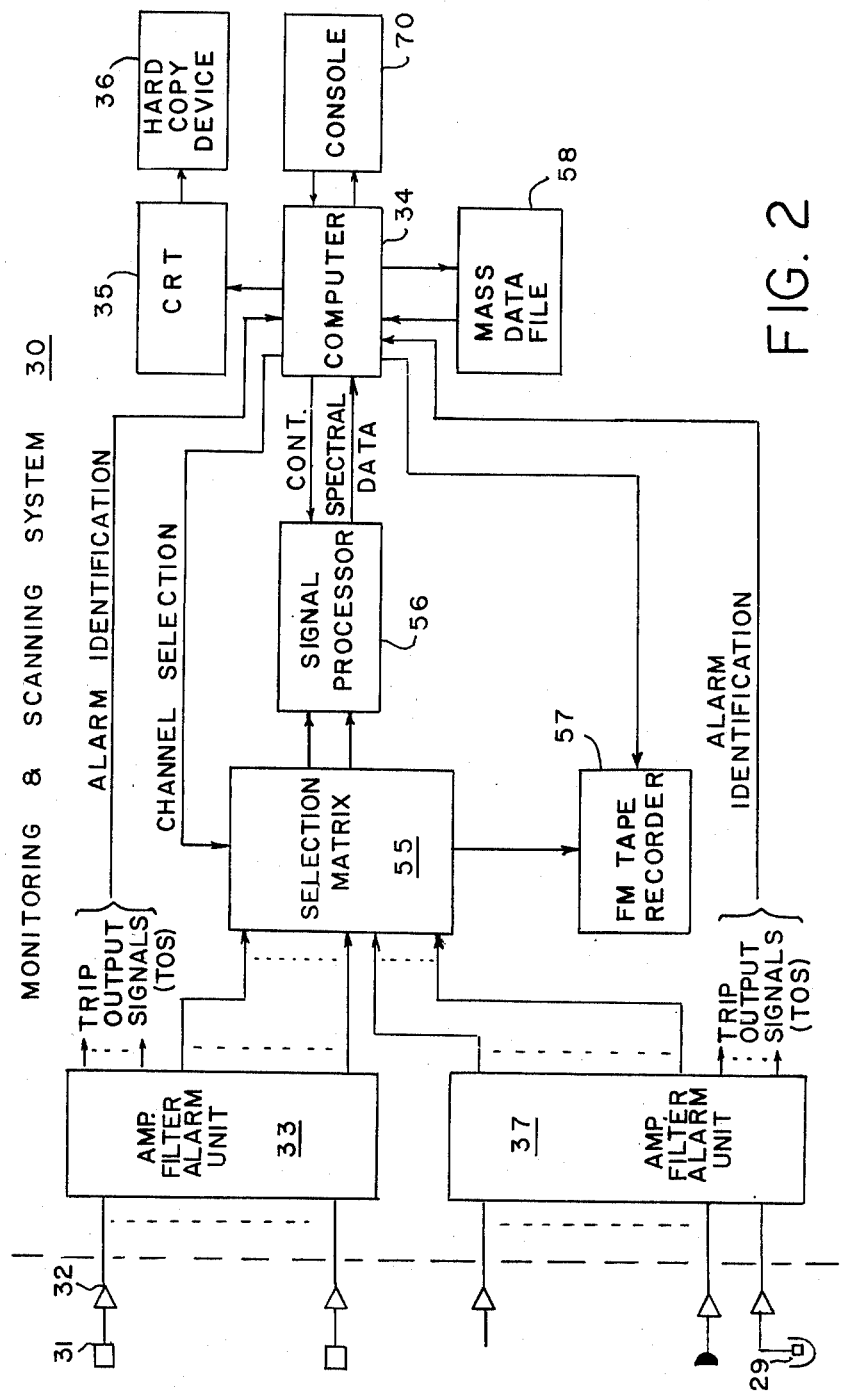
FIG. 2 is a block diagram of the automatic monitoring and scanning system shown in FIG. 1.

Referring now to FIG. 2, a vibration sensor 31 is shown coupled by its preamplifier 32 to a channel of an amplifier filter alarm unit 33. Each sensor has its own channel in the unit 33 such that the signal from each sensor is continually being amplified, filtered and tested for certain alarm conditions which produce "trip output" signals to a programmed digital computer 34. Each such signal received by the computer 34 causes the computer to branch into a subroutine to effectively test each sensor to determine whether it has created a "trip output" signal. If so, the computer identifies the source of the alarm condition, displays the information on a cathode ray tube 35 and produces a hard copy of the same information displayed on the CRT through a device 36. At the same time, a visual alarm (light) is energized to indicate which channel has the alarm condition, and an audio alarm is energized to call the operators attention to the fact that an alarm condition has been reached.

A similar amplifier filter alarm unit 37 is provided for other types of sensors such as the neutron flux sensor 29 to determine when an alarm condition has occurred, sound the alarm and turn on the channel light. A "trip output" signal is coupled from each channel of the unit 37 to the computer 34 in order that a separate subroutine of the program for the computer determine which channel has the alarm condition and to display the information through the CRT and hard copy device.

Figure 3:
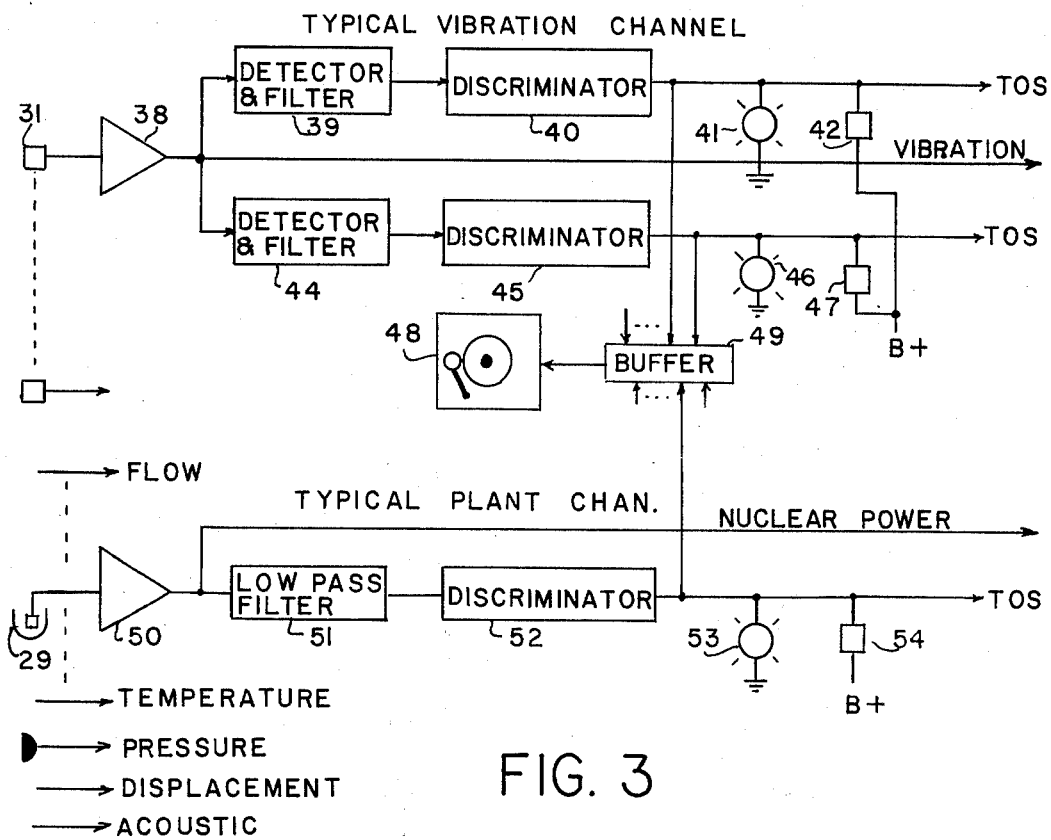
FIG. 3 is a schematic diagram of a typical vibration monitoring channel.

FIG. 3 illustrates a typical channel in the unit 33 for a vibration sensor and a typical channel for another type of sensor in the unit 37. The vibration sensor 31 and neutron flux sensor 29 have been selected as representing the typical sensors of each type. In the vibration channel, the signal is first amplified through an amplifier 38 and then passed through a detector and filter 39 to a discriminator 40. The output of the detector and filter 39 is a DC signal the amplitude of which is a function of vibration frequency and amplitude. Should the frequency and/or amplitude exceed a predetermined limit, the DC output of the detector and filter will produce a "trip output" signal from the discriminator 40. That signal turns on a light 41 and sets a latching switch 42 which then connects the light 41 to a source of power (B+) to maintain the light until the switch is reset upon the operator responding to the vibration alarm.

The vibration signal from amplifier 38 is also passed through a detector and filter 44 for loose parts monitoring. The filter characteristics are designed to produce an output signal above a predetermined amplitude only when impact signals (normally of higher frequency and lower amplitude) are present. When the level has been exceeded, a discriminator 45 turns on a light 46 and sets a relay 47. All of the "trip output" signals from vibration channels are coupled to an audio alarm 48 through a buffer 49 to sound an alarm.

Channels in the unit 37 (FIG. 2) for other types of sensors are very similar to channels in the unit 33 as shown in FIG. 3. The output of an amplifier 50 is coupled by a low pass filter 51 and the filtered output is applied to a discriminator 52 which determines when a predetermined amplitude has been exceeded. At that time a light 53 is turned on and an alarm relay 54 is set. The "trip out" signal from the discriminator 52 is applied to the audio alarm 48 through the buffer 49, as well as to the computer 34 (FIG. 2).

Referring to FIG. 2, the output signal of the amplifier in each channel of the unit 33 and the unit 37 is coupled through a separate cable to a selection matrix 55 which, under control of the computer 34 selects which signal output is to be applied to a signal processor 56 and/or an FM tape recorder 57 for PSD analysis or recording. Under normal operation, the computer will sequentially scan the signal outputs in a predetermined order for PSD analysis. The computer will also be able to turn on the FM tape recorder in order to record the analog signal from the sensor.

When an alarm condition produces a "trip output" signal, the computer may be interrupted and caused to branch from its normal scanning pattern to select the channel producing the trip output signal for PSD analysis and tape recording. However, in the case of a "trip output" signal from the unit 37, the signal processor 56 is effectively turned off and the channel signal is passed straight through with only analog-to-digital conversion under control of the computer 34 to record just the signal producing the "trip output" alarm unless PSD analysis of such a signal is required.

Considering only output signals from vibration sensors, and omitting from further discussion the loose parts monitoring function of each channel, it should be noted that normal operation of the monitoring and scanning system is to sequentially connect the signal outputs of unit 33 to the signal processor 56 for PSD analysis under control of the computer. The spectral data developed by the signal processor 56 is received by the computer and further processed to find potential malfunctions.

In some cases it is desirable to analyze the relationship between two channels so that events that are being sensed by two separate sensors may be correlated. That is accomplished under control of the computer by selecting two channels, such as by setting a separate one-pole, N-position switch to connect a second channel to the processor 56. The signal processor would then be set to perform cross product calculations, which is a variation on the simple Fourier transform calculations, to analyze the cross PSD between the two channels. Fast Fourier transform processors capable of performing either the simple or the cross PSD calculations on command are commercially available from several sources.

In the case of cross PSD calculations, the cross product calculation performed between the two selected channels can be used not only to obtain a cross spectral plot (cross correlation plots in the time domain), but their transfer functions also. Amplitude, phase and coherence plots would be obtained from the transfer function calculations as well. These plots then could be used to diagnose the condition of various components related to the channels from which these plots were obtained.

While only vibrations have been referred to specifically, other types of physical conditions may be monitored by sensors just as vibrations are monitored by accelerometers to produce dynamic electrical signals, particularly those conditions closely related to vibrations. For example, pressure in a coolant line may be monitored since the dynamic variations of pressure in many cases can be the driving function of the vibration. Cross PSD analysis of the pressure function and the vibration function can be of value in analyzing any anomaly present in the coolant line. A similar relationship can be found between two of the reactor plant channels which measure neutron flux leakage from the core (only one is shown in FIG. 1). Cross PSD analysis between these channels can be used to infer core vibrations which could not be sensed by conventional vibration sensors.

An example of cross PSD monitoring is in connection with a charging pump in a nuclear power station. Generating pressure pulsations cause movement in the core. A simple cross product (cross PSD) analysis of a pressure sensor for the charging pump and a vibration sensor for the core would then indicate the cause of the core motion and give the operator an indication of what action to take, such as to check the charging pump to remove the cause of the core motion.

An example of a single channel PSD analysis is in connection with a reactor recirculation pump cavitating because of a particular pressure condition existing at the pump. The dynamic condition signal took the form of an increasing spectral content at higher frequencies. The sampling period for the signal is selected to provide an adequate number of samples of the spectral content at the lowest frequency of interest in the signal from the particular sensor. Typical sampling periods for sensing vibrations in a nuclear power plant range from 1 to 120 seconds. The normal PSD plot associated with the recirculating pump takes the form of a decreasing spectral content at higher frequencies. This gives a very unique PSD plot for the pump while it is cavitating. The present invention would quickly detect this unique plot, diagnose the condition and indicate to the operator the action to take.

Because of the many points that require monitoring in an operating plant, the many potential malfunctions and the many causes, it is essential that all points be very rapidly scanned and analyzed. An operator could not be expected to scan all of the points in real time under manual control and also perform the analysis, even with a signal processor for automatically developing the PSD data. An automatic monitoring and scanning system enhanced by the automatic diagnosis and indication of action to be taken, all in real time, in accordance with the present invention, will greatly increase the effectiveness of an operator and insure much greater safety than is otherwise possible.

It should be noted that in the loose parts detection function of the system, the occurrence of a loose parts signal is detected to cause an appropriate message to be displayed on the CRT. It also causes the FM tape recorder to be turned on and to record the output of the sensor from the channel in which the loose parts event has been detected to preserve the signal from the loose part. It should be noted that a standard vibration and loose parts monitor has this same capability, i.e., it also can cause a tape recorder to be turned on and the appropriate tape recording channel selected to perform the same recording function. In that case the use of a computer in the system does not significantly enhance the performance capabilities. It is only in the PSD analysis and diagnosis function of the present invention that the use of a computer significantly enhances performance capabilities.

Any potential malfunction is found automatically by the computer based on comparison of PSD data with frequency dependent limits stored in a table in the memory section of the computer or a mass data file 58. In the latter case, the computer looks up the table and copies it into temporary memory in the computer. The transfer is made while the PSD data is being developed for the particular channel. Looking up the appropriate table is merely a matter of converting the channel number to an address code for the first of a block of memory word addresses in the mass data file. As each word of the table is copied, the address is incremented until a predetermined number of words have been copied into the computer. The table also includes diagnostic and action data. When a frequency dependent limit is found to be exceeded by the channel PSD data, the condition indicated in the table is displayed on the CRT and copied by the hard copy device. For each condition, there is also a corresponding action indicated in the table. That action is also displayed on the CRT and copied by the hard copy device. The following is an example of the diagnostic information displayed for one complete cycle of 32 channels four of which are spares not in use.

| CHAPTER 0000 | PAGE 0043 | YEAR 1975 | DAY:HR:MIN:SEC = 0105:17:30:03 |
|---|---|---|---|
| CH CHAPTER NAME | | CONDITION | ACTION |
| 01 LOWER VESSEL | | MID FREQ. NOISE | LISTEN, INSPECT NOW |
| 02 LOWER VESSEL | | HIGH FREQ. NOISE | LISTEN, INSPECT NOW |
| 03 UPPER VESSEL | | HIGH FREQ. NOISE | LISTEN, INSPECT NOW |
| 04 UPPER VESSEL | | HIGH FREQ. NOISE | LISTEN, INSPECT NOW |
| 05 RC PUMP 1-1-1 | | PUMP SEAL | INSPECT PUMP SEALS |
| 06 RC PUMP 1-1-2 | | NORMAL | NONE |
| 07 RC PUMP 1-2-1 | | PUMP NOISE | CHECK PUMP |
| 08 RC PUMP 1-2-2 | | HIGH FREQ. NOISE | INSPECT PUMP INST. |
| 09 SG 1-1 UPPER | | HIGH FREQ. NOISE | LISTEN, CHECK SG INST. |
| 10 SG 1-1 LOWER | | STRUCTURE MOTION | CHECK FOR SG MOTION |
| 11 SG 1-1 UPPER | | LOW FREQ. NOISE | CKECK SG NOISE |
| 12 SG 1-2 UPPER | | MID FREQ. NOISE | INSPECT SG INST. |
| 13 CORE INT NI-5 | | CORE NOISE | CHECK FOR CORE MOTION |
| 14 CORE INT NI-6 | | NORMAL | NONE |
| 15 CORE INT NI-7 | | CORE NOISE | INSPECT CORE |
| 16 CORE INT NI-8 | | NORMAL | NONE |
| 17 CTMT AIR COOL.1-1 | | STRUCTURE MOTION | CHECK FAN |
| 18 CTMT AIR COOL.1-2 | | NORMAL | NONE |
| 19 CTMT AIR COOL.1-3 | | STRUCTURE MOTION | CHECK FAN |
| 20 ACOUSTIC RCP1-1-1 | | NORMAL | NONE |
| 21 ACOUSTIC RCP1-1-2 | | NORMAL | NONE |
| 22 ACOUSTIC RCP1-2-1 | | MID FREQ. SOUND | LISTEN TO CHANNELS 7&8 |
| 23 ACOUSTIC RCP1-2-2 | | HIGH FREQ. SOUND | LISTEN TO CHANNELS 7&8 |
| 24 ACOUSTIC PRZR | | HIGH FREQ. SOUND | LISTEN TO ALL CHANNELS |
| 25 RCS PRESSURE | | NORMAL | NONE |
| 26 MAKE UP PUMP 1-1 | | NORMAL | NONE |
| 27 MAKE UP PUMP 1-2 | | NORMAL | NONE |
| 28 AUXILIARY | | NORMAL | NONE |
| 29 SPARE | | NORMAL | NONE |
| 30 SPARE | | NORMAL | NONE |
| 31 SPARE | | NORMAL | NONE |
| 32 SPARE | | NORMAL | NONE |

There are two upper and two lower vessel vibration sensing channels, although only two are shown in FIG. 1. Each recirculating (RC) pump is equiped with one vibration sensing channel. The four recirculating pumps shown in FIG. 1 are assigned unique code numbers for identification. The vibration sensing steam generator (SG) channels (one for each upper and lower vessel) are also assigned unique code numbers as shown in the display. The next four channels 13 through 16 for monitoring core internals (sensors not shown in FIG. 1) yield core dynamic information. The sensor signals are typically 0 to 10 volt for 0 to 125% power operation with a bandwidth of at least 20Hz. The next three channels 17 through 19 are for low temperature accelerometers for sensing vibrations on the containment (CTMT) air cooler motor frames near the fan blades. Channels 20 through 24 are for dynamic microphones located inside the plant containment, such as one near each recirculating pump and one near a pressurizer (not shown in FIG. 1), each with a bandwidth of 50Hz to 15kHz. Channel 25 is a core pressure channel (sensor not shown in FIG. 1), and is similar to the core internals channels. Channels 26 and 27 are for low temperature accelerometers for sensing vibrations of two make up pumps. The auxiliary channel 28 is provided as a complete additional channel connected to a vibration sensor that can be easily mounted on any piece of equipment in the plant for loose parts and vibration monitoring.

The conditions indicated in the foregoing example of a 32-channel display are merely for illustration only. In practice there would not be so many potential malfunctions indicated because failures are rare and as each potential malfunction is found, it is corrected. The actions indicated are also only exemplary. In practice more specific instructions may be indicated, particularly as more is learned about the plant equipment by experience. When plant installation is first completed, a baseline PSD and the table of frequency dependent limits, conditions and actions are stored for each channel. The table is derived from information gathered from suppliers of components and from experience in other similar plants. The table is thereafter used in monitoring actual plant operation, and is refined as it is used to eliminate false malfunction indications and include others not originally included. That is done with experience by adding or altering frequency dependent limits and associated condition and action indications.

Figure 4:
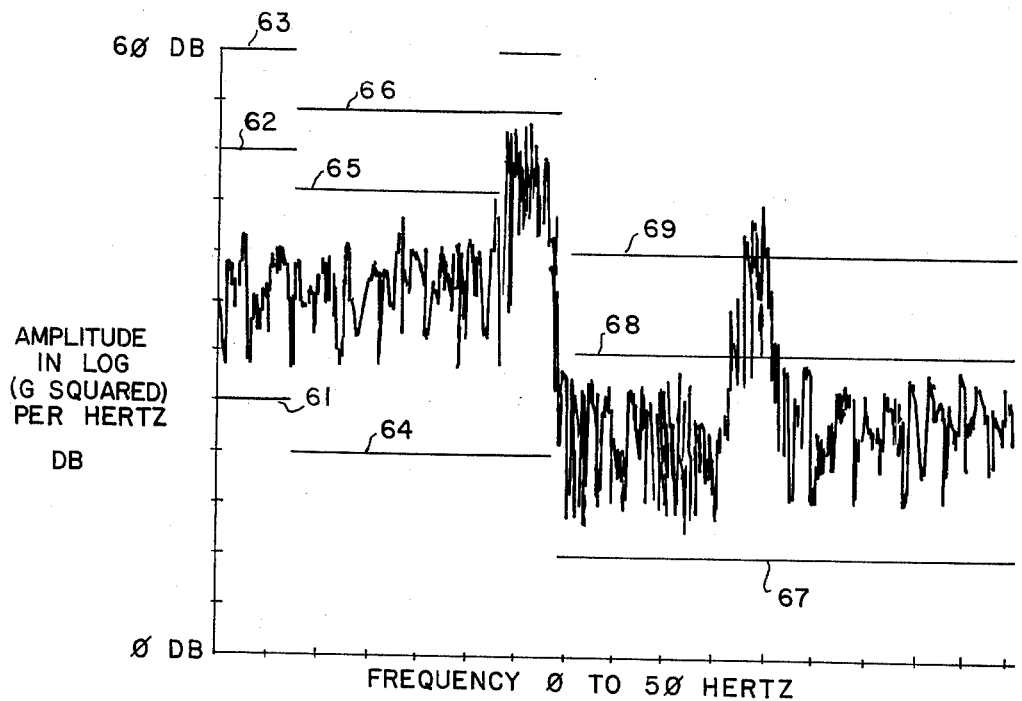
FIG. 4 is a graph of the power spectral density (PSD) of the typical channel shown in FIG. 3 illustrating exemplary frequency dependent limits used in diagnostic analysis.

FIG. 4 illustrates a PSD graph for one channel with four sets of frequency dependent limits used in a manner to be described more fully hereinafter. The PSD data is, of course, in digital form so that limit tests can be performed by the computer and so that the data may be stored in the mass data file 58 for comparison with a later PSD data to detect significant changes and the rate of changes or trends. The limit tests performed on the PSD data of a channel will indicate whether particular components are normal, and if not whether the abnormality merely requires caution or some immediate action. For example, at the lower end of the spectrum illustrated in FIG. 4, a first level 61 must be exceeded. Failure to do so may be an indication of some impending failure which will bear watching, but which presents no problem until such time. However, a higher limit 62 should not be exceeded. At any time it is found to be exceeded by an excursion below a level 63, a diagnostic message is displayed indicating that a bad condition is present and indicating as the action to be taken to inspect the particular component associated with this channel, such as a coolant pump. If the upper limit 63 is exceeded, the condition indicated might be critical and the action indicated might be to check the component immediately.

The next higher frequency range is also provided with three limits. The first, limit 64, is so low as to be normally exceeded throughout, thus indicating that the condition of a related component, such as the pump seals is normal. Should the next level 65 be exceeded, the diagnosis might be an impending failure with appropriate action indicated, such as to check pump seals for leakage. The upper limit 65 would indicate a critical condition with the action indicated to replace the seals.

The next frequency range, a narrow range, has a lower limit the same as the limit 64 for the pump seals, a higher limit the same as the critical limit 66 for the pump seals, and a still higher limit equal to the limit 63. This particular frequency range may be, for example, associated with structure motion of the pump installation such that the level 64 indicates normal operation, while the level 66 indicates some impending failure which would require checking the fan installation. The higher level would then indicate a more critical condition requiring immediate replacement or repair of the pump support structure.

Figure 5:
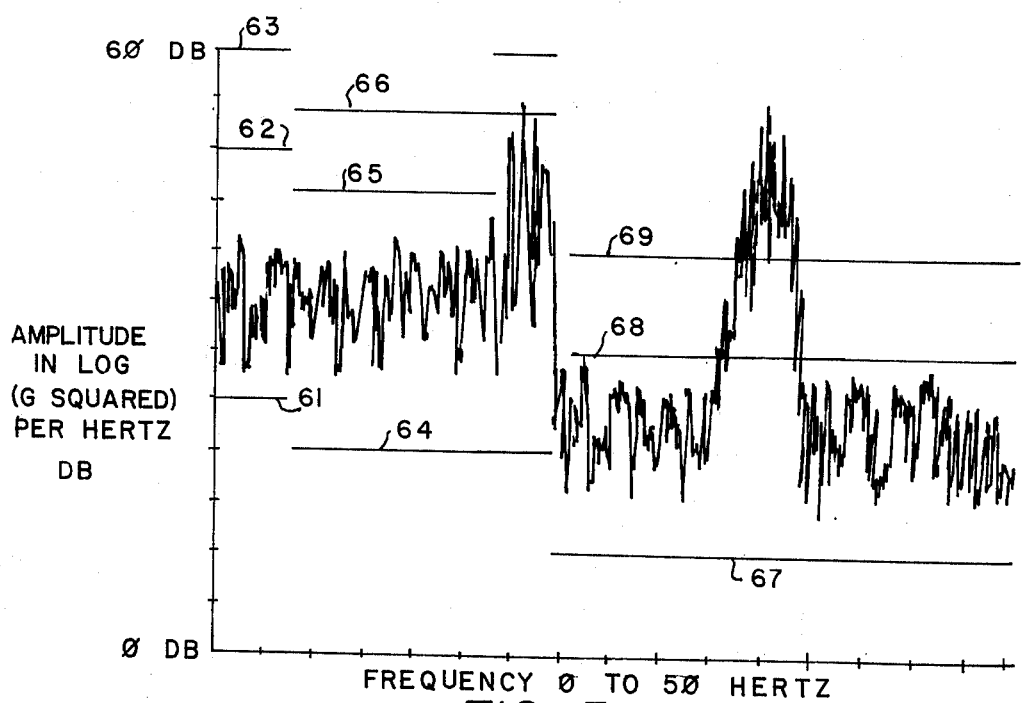
FIG. 5 is a graph of the PSD for the same channel as for the graph of FIG. 4 illustrating a deteriorated condition of the plant at a later time.

The balance of the PSD represents normal pump noise so that a lower limit 67 is provided to determine that the pump is in operation. The next higher level 68, the upper bound of normal pump noise, will indicate deteriorating pump bearings that will require replacement during the next scheduled preventive maintenance, particularly if, when compared with a subsequent PSD shown in FIG. 5, it is seen that this limit 68 is being exceeded by more than in the earlier PSD of FIG. 4. An upper limit 69 indicates when the condition has become so critical as to require more immediate action, but diagnostic analysis of the PSD should require that this level be exceeded during more scanning cycles than just the one indicated at FIG. 5, particularly since the peak which does exceed that level in the PSD of FIG. 5 is not present throughout the frequency range of the limit 68.

Figure 6:
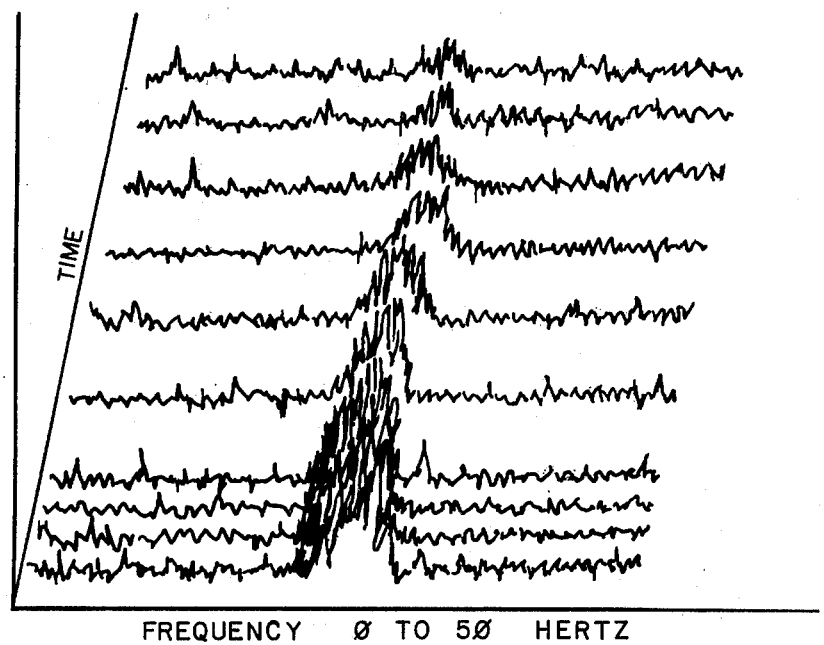
FIG. 6 is a typical sequential display of successive PSD records for the same channel illustrating the onset and subsidence of an exaggerated anomalous condition.

To aid in the diagnosis, any frequency range of a PSD may be selected for display on the CRT 35 with the same frequency ranges of previous PSDs as shown in FIG. 6 with the four most recent ones in the foreground and, for example, every other one of earlier PSDs in the background, all in successive order with the most recent at the bottom and each successively earlier one displaced to the right to provide a pseudo three dimensional display that will quickly show the operator any trend. In this case the display indicates the random noise of a pump throughout the range monitored by the level 68 as shown in FIGS. 4 and 5 and shows the growing trend of the anomaly shown in FIGS. 4 and 5. The time at which the critical level 69 will be exceeded can be quickly estimated by the operator and more accurately determined by the computer, as by a subroutine called out by the operator from a console keyboard for a trend analysis.

A trend analysis would be performed by taking data in each of the frequency intervals of a PSD plot used for particular limit analysis and averaging the data over that particular interval for any one scan cycle to obtain an average value over that interval that is stored as histoical data. The historical data would then be used to perform a trend analysis by taking the averaged value of the sample in any one frequency interval and doing a regression analysis to fit the best trend line to that data. If that trend line shows a significant slope in the way of an increasing or decreasing value over a period of time, it would be indicative of a significant trend and would be used to alert the operator to the fact that the data in the particular interval is showing this trend, and indicate appropriate corrective action.

In addition to the use of this automatic monitoring and scanning system on nuclear power stations, other types of power stations, for example, coal-fired power stations, could use the system to equal advantage. The system would be applicable to chemical processes and other industrial applications that use pumps for circulating fluids, and to potentially all sorts of other plants. A refinery, for example, would have circulating fluids and pumps, and certainly changes in the makeup of these would be of interest. In a molten salt coal gasification process a vibration sensor on the reaction vessel will be used to obtain a PSD plot and from an analysis of the PSD plot an index of the viscosity of the melt in the gasification rig. That data provides a criteria by which an operator could vary the makeup and discharge of the molten salt as it becomes too viscous to economically pump the mix through. It would, of course, be possible to provide a closed control loop to maintain viscosity constant. That is well within the state of the art of computer control over an industrial process. What is new is the automatic scanning of the vibration sensor and obtaining PSD data of the sensor signal for analysis.

In operation, the computer program compares the gross amplitude of the PSD signal at different frequencies against predetermined limits to detect the normal or abnormal condition of an operating plant. The plant is here illustrated as a nuclear steam generating plant for an electrical generator but, as noted hereinbefore, it may be an industrial plant. Normally there are no loose parts in a plant, so the output of the loose parts channel of each vibration sensor is normally quite low, such as near zero. Thus there is inherent in the vibration monitoring and scanning system a capability of detecting loose parts quite easily. What is more difficult is finding potential malfunctions. For that the system relies upon power spectra of vibration and other dynamic signals.

The dynamic signal from each sensor is composed of many different mechanical actions or processes going on within the plant, most of which have unique frequencies associated with them. The core barrel, for example, vibrates at one frequency while the control rod is so structured as to vibrate at some other frequency. By programming the computer to look at the spectrum of these events with respect to just amplitude as a function of frequency, the condition of each is found separately by looking at unique peaks found in the sensor signal. However to monitor the core and the rod separately, it is necessary to employ a greater level of specification in measurements. This is done through power spectral density measurements taken by connecting the output of the sensor into the signal processor 56 (FIG. 2) for power spectrum analysis. In practice the signal processor includes a spectrum analyzer that is commercially available, such as one based upon a fast Fourier transform algorithm.

The signal processor provides in digital form a power measurement which can be plotted in amplitude as function of frequency over whatever range is selected for the operation. By looking at this power spectral density (PSD) against predetermined limits, it is possible to recognize that a specific characteristic frequency may have changed in amplitude to exceed predetermined limits or to have changed in frequency. These changes could be attributed to, for example, some change in the damping of a particular part by some structural member breaking, as has occurred in at least one actual plant. There are other recognizable factors which could change the frequency of the sensor signal such that the PSD peaks would shift either in amplitude or in frequency.

To facilitate analysis of potential malfunctions by comparison of PSDs with frequency dependent limits, a baseline PSD is obtained from each sensor signal when it is known that the plant is operating normally with all components in good condition. Different PSDs may then be obtained for a given sensor with different possible malfunctions simulated or deliberately introduced momentarily. Limits can then be set for different frequency ranges and an appropriate action stored in the computer in association with each limit. Once this basic information is obtained and stored in the computer, the operator may alter these limits and/or the associated statements of action indicated, from experience. If done judiciously, this technique for predicting potential malfunctions can be refined to a very high degree. For example, if frequency noise on a pump bearing indicates a potential malfunction, but the level of frequency noise stabilizes, the limits for that pump may be widened.

Another source of information useful in determining limits, at least at the outset, is the data supplied by the manufacturer of the component parts, such as the various pumps. However, the data thus supplied should be compared against the actual data after initial installation to ascertain the effect the particular installation may have on the data, particularly the supporting structure. In any case, the initial setting of limits may be but a first step in a learning process that is aided very significantly by the infallible memory of the computer.

Specifically, the operation of the scanning and monitoring system is as follows. The computer is scheduled in its tasks by a real-time clock. A stored executive program directs the computer to perform various tasks at specified times or timed intervals. Iterative execution of this executive program which calls out subroutines as necessary is the normal mode of operation of the system. The computer may be interrupted from this mode of operation if an abnormal condition is detected in the plant, as by the loose parts monitoring channels or by the PSD analysis channels. In other words, the executive program will periodically respond to the real-time clock to cause a subroutine to be called out for scanning the sensor signals through the selection matrix 55. Typically there may be anywhere from eight to several hundred signal outputs to be sequentially scanned and processed by the signal processor 56. Each signal scanned may also be recorded on the FM tape recorder, as noted hereinbefore. The signals from these sensors are continually monitored for loose parts and checked in gross amplitude to determine the presence of any malfunction as described hereinbefore with reference to FIG. 3. The improvement in the scanning and monitoring system resides in analyzing the PSD of each sensor signal in respect to frequency dependent amplitude limits.

The computer 34 controls the signal processor in selecting a frequency range over which the spectrum analysis is to be carried out for the particular sensor signal. When the spectrum analysis is completed for a given signal, the signal processor interrupts the computer and the computer receives the PSD in digital form, i.e., in the form of a digital value equal to the scaled amplitude of the PSD as a function of frequency. Typically a PSD may include 256 equally spaced frequency points, and the amplitude at each point is quantized to one part in 1024 for a resolution that is essentially one tenth of one percent in amplitude.

This PSD data in digital form is then compared with numerical limits in a table, either in the computer memory itself or in the mass data file 58. In either case, the operator can set or alter these limits through a console keyboard 70. The particular family of limits chosen for a particular sensor signal can be typically plotted over 32 discrete intervals covering the PSD. These intervals can have arbitrary beginning and ending points in frequency, and for each of these intervals, three limit values may be set. One is a low limit which, for example, should be exceeded. Should the PSD being analyzed fall below this limit, a malfunction would be indicated and a diagnostic message would be displayed on the CRT 35 and the hard copy device 36 to the effect that the signal has been lost and that operation of some device should be checked, such as "check to see if motor No. 3 is on." The next level could be an alert level, that is to say the first degree of operating abnormality. The third level would then be an alarm level which indicates the frequency dependence amplitude of the PSD has grossly exceeded normal operating limits. In other frequency intervals, the first (lower) level may be the caution level if exceeded while the next is an abnormality level and the third is an alarm level. In either case, for each comparison level some diagnostic information is displayed on the screen of the CRT and the hard copy device.

The message display is in the form of a tabular listing giving channel (sensor number), channel identification, the nature of the abnormal event that has been detected, and the corrective action indicated for the operator to take to either further define the nature of the abnormality or to correct the abnormality. The nature of these messages is such that they can be changed if, in the judgment of the operator, they do not adequately describe the situation or, it is determined from experience that they do not accurately describe the situation. Thus, as more information is developed about the plant, the message information may be easily changed through the console keyboard just as the limits themselves may be changed.

In practice, the limits and the diagnostic information would be stored in the computer memory in order to facilitate executing the sequence of instructions necessary to make the limit comparisons and select for display the appropriate diagnostic information. However, in the event there is insufficient memory in the computer to store all of the information, it would be possible to store it in the mass data file and to read it into the computer for each channel as it is scanned in sequence, as indicated hereinbefore. Thus, while the signal processor 56 is carrying out the necessary computations to develop the PSD for the channel, the computer may be reading into computer memory the table of limits and diagnostic messages for that channel from the mass data file.

In a preferred embodiment the mass data file is also used to store complete PSD scans for all channels over a selected interval of from one hour to as much as one year or even more. It is then possible to retrieve this information from the mass data file to compare it with the current data and thus determine any changes and the rate of changes and trends. In practice, a subroutine to recall this data from the mass data file for this purpose would be under operator control. At any time that an alarm is indicated, or there is a diagnostic message of a serious nature, the operator would be able to call for CRT display in a pseudo three dimensional form as shown in FIG. 6 of a frequency interval of interest in prior PSDs for comparison. Alternatively, the operator could call for CRT display of only the current PSD with the limits indicated as shown in FIG. 4. Following that, he could call for a particular prior PSD, such as one taken an hour ago, to be displayed superimposed over the current PSD so that he may compare the two spectra to determine the change which has taken place. He could make specific comparison with successively earlier PSDs to determine the rate of change and the trend, and for a final overview, display all of the prior PSDs with the current one in the pseudo three dimensional form of FIG. 6.

The following flow charts illustrate the more fundamental subroutines employed. All may be readily executed by any scientific computer, or industrial process control computer. A computer Model PDP 11 manufactured by Digital Equipment Corporation is typical.

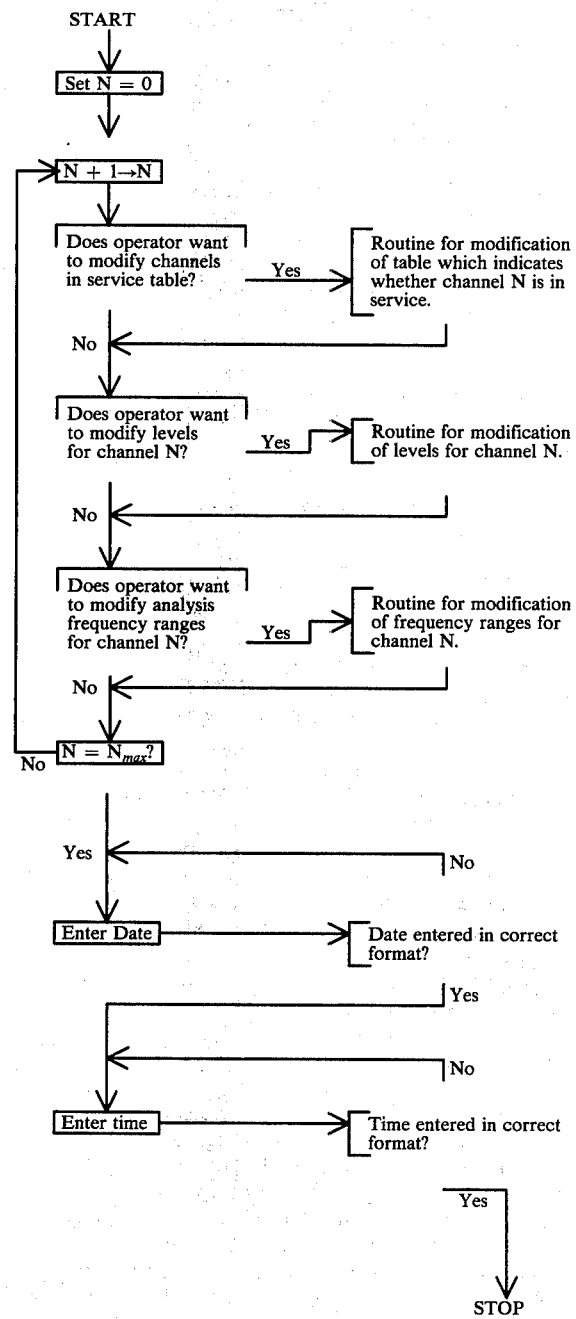

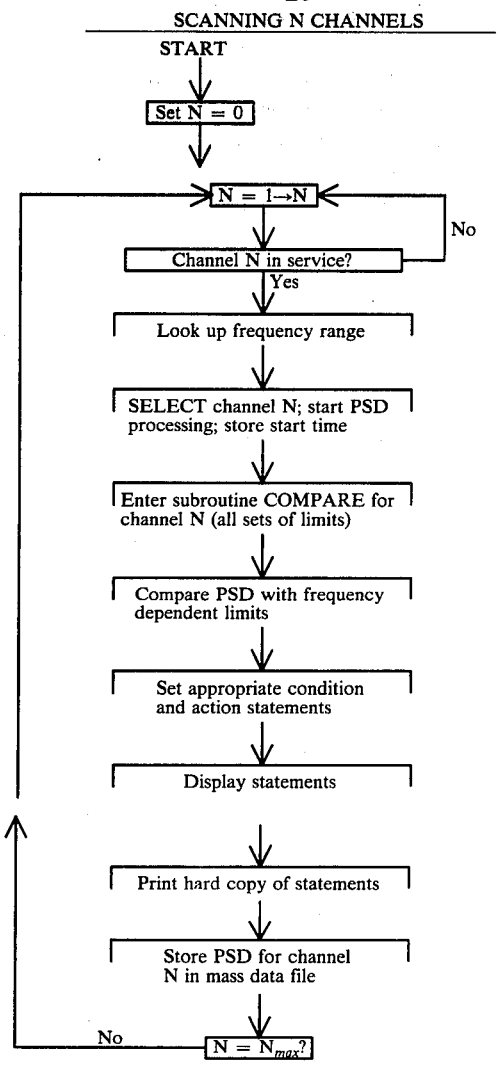

The daily service routine provides for entering the date and the correct time at the beginning of the first shift of each day. The real-time clock of the computer accepts the time entered as the correct time from which time is thereafter reckoned. At this time the operator has the option to modify the table of channels in service, to modify the test levels for the various channels and/or to modify the frequency ranges for the test levels of the various channels.

Once the daily service routine has been completed, the operator may initiate the scanning routine from the console. The scanning routine stops when all N channels have been scanned, but is automatically started again at predetermined times, or intervals of time, as set in an executive routine.

Although particular embodiments have been disclosed and described, it should be understood that equivalent embodiments and modifications are also contemplated, particularly in the respects already indicated of automatic analysis of the power spectra of any dynamic signals (time dependent fluctuating signals generally) in any operating plant, and in respect to cross correlation of power spectra of selected dynamic signals, including the maintenance of a historical file of power spectra in each dynamic signal for comparison, all for the purpose of finding potential malfunctions, drawing conclusions as to their severity, and indicating to the operator what action to take. Consequently, it is intended that the claims be interpreted to cover such modifications and equivalents.

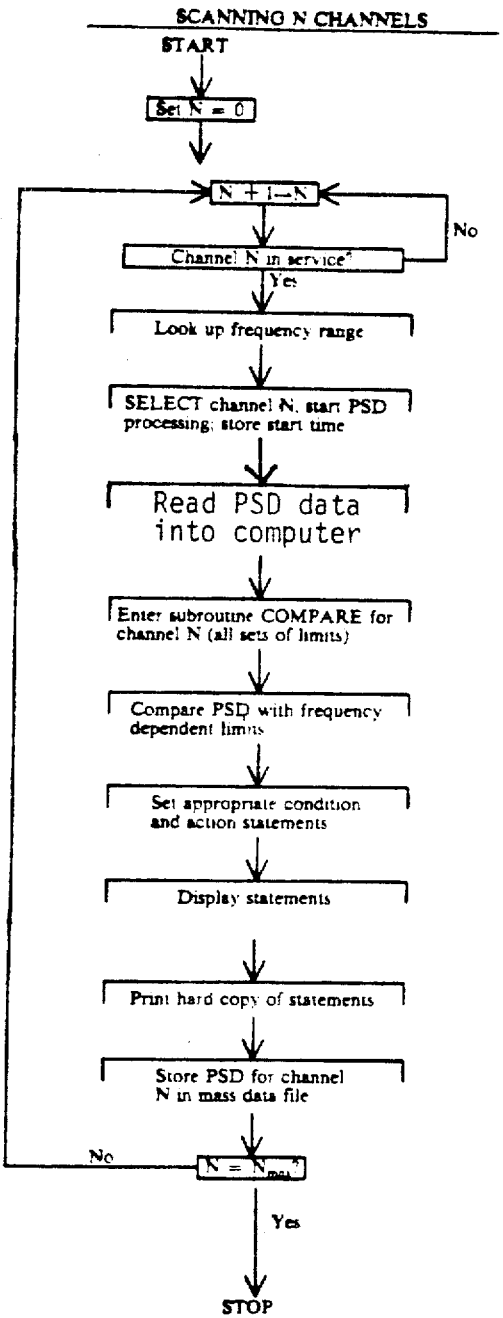

What is claimed is:

1. In an operating plant having significant background noise in time dependent fluctuating signals derived from sensors placed at selected points for continually monitoring the operating conditions of system components, a method for scanning in real-time separate signal conditioning channels, one for each of said signals, to find potential malfunctions, draw conclusions as to their severity and indicating to an operator what action to take comprising the steps of:

selecting each channel in sequence for spectral analysis;

processing the signal of each channel selected to produce power spectral density data at predetermined frequencies over a predetermined frequency range as a simple Fourier transform;

comparing said power spectral density data of each channel with predetermined sets of frequency dependent limits, each set consisting of at least two limits, one for a condition requiring caution, and another for an alarm condition requiring more direct action by the operator; and indicating to the operator the condition of plant components associated with each channel and the action to be taken as a function of which set of limits and which limit of the set is exceeded by said power spectral data.

2. A method as defined in claim 1 wherein two paired channels are selected simultaneously in place of a selected single channel, and wherein the step of processing the signal of the paired channels selected is modified to produce cross power spectral density data as a variation on the simple Fourier transform for analysis of the relationship between the paired signals.

3. A method as defined in claim 2 wherein one of said paired channel signals is a vibration signal from a sensor mounted on a fluid handling component, and the other one of said paired channel signals is a pressure signal from a transducer responsive to the pressure of said fluid.

4. A method as defined in claim 1 wherein at least one set of frequency dependent limits for a selected channel includes three levels: a first one of which must be exceeded for a normal equipment operating condition to be indicated; a second one of which must be exceeded for an alert condition to be indicated; and a third one of which must be exceeded for an alarm condition to be indicated.

5. A method as defined in claim 1 wherein at least one set of frequency dependent limits for a selected channel includes three levels: a first one of which must be exceeded for a caution condition to be indicated; a second one of which must be exceeded for an alert condition to be indicated; and a third one of which must be exceeded for an alarm condition to be indicated; said levels thus being spaced apart to indicate different degrees of severity in a potential malfunction and different actions to be taken when exceeded.

6. A method as defined in claim 1 including the step of storing power spectral density data from each channel in a historical file, and the step of calling up the power spectral density data for a selected channel from at least one prior scan for comparison of power spectraldensity data derived from a single channel at different times for determining any change.

7. A method as defined in claim 6 including the step of displaying power spectral density data of selected prior scans for visual comparison.

8. A method as defined in claim 7 wherein the power spectral data displayed is for only a selected frequency range of interest.

9. A method as defined in claim 1 wherein said indication of condition and action to be taken is determined on the basis of a stored table based upon prior experience as to malfunctions and known characteristic spectra of operating components.

10. A method as defined in claim 9 including the step of updating said table periodically on the basis of experience since the last time of updating said table.

11. In an operating plant having significant background noise in time dependent fluctuating signals derived from sensors placed at selected points for continually monitoring the operating conditions of system components, apparatus for scanning in real-time separate signal conditioning channels, one for each of said signals, to find potential malfunctions, draw conclusions as to their severity and indicating to an operator what action to take comprising a computer and including:
computer controlled means for automatically selecting each channel in sequence for power spectrum density analysis;
computer controlled means for automatically processing the signal of each channel selected to produce power spectral data at predetermined frequencies over a predetermined frequency range as a simple Fourier transform;
means within said computer for automatically comparing said power spectral density data of each channel with predetermined sets of frequency dependent limits, each set consisting of at least two limits, one for a condition requiring caution, and another for an alarm condition requiring more direct action by the operator; and
computer controlled means for automatically indicating to the operator the condition of plant components associated with each channel and the action to be taken as a function of which set of limits and which limit of the set is exceeded by said power spectral density data.

12. Apparatus as defined in claim 11 wherein said selecting means selects two paired channels simultaneously in place of a selected single channel, and wherein the means for automatically processing the signal of the paired channels selected is automatically modified by said computer to produce cross power spectral density data as a variation on the simple Fourier transform for analysis of the relationship between the paired signals.

13. Apparatus as defined in claim 12 wherein one of said paired channel signals is a vibration signal from a sensor mounted on a fluid handling component, and the other one of said paired channel signals is a pressure signal from a transducer responsive to the pressure of said fluid.

14. Apparatus as defined in claim 11 wherein at least one set of frequency dependent limits for a selected channel includes three levels: a first one of which must be exceeded for a normal equipment operating condition to be indicated; a second one of which must be exceeded for an alert condition to be indicated; and a third one of which must be exceeded for an alarm condition to be indicated.

15. Apparatus as defined in claim 11 wherein at least one set of frequency dependent limits for a selected channel includes three levels: a first one of which must be exceeded for a caution condition to be indicated; a second one of which must be exceeded for an alert condition to be indicated; and a third one of which must be exceeded for an alarm condition to be indicated; said levels thus being spaced apart to indicate different degrees of severity in a potential malfunction, and different actions to be taken when exceeded.

16. Apparatus as defined in claim 11 including means for automatically storing power spectral density data from each channel in a historical file, and means for calling up the power spectral density data for a selected channel from at least one prior scan for comparison of power spectral density data derived from a single channel at different times for determining any change.

17. Apparatus as defined in claim 16 including means for calling up and displaying power spectral density data of selected prior scans.

18. Apparatus as defined in claim 17 wherein the power spectral density data displayed is for only a selected frequency range of interest.

19. Apparatus as defined in claim 11 wherein said indication of condition and action to be taken is determined on the basis of a stored table based upon prior experience as to malfunctions and known characteristic spectra of operating components.

20. Apparatus as defined in claim 19 including a computer console means for updating said table periodically on the basis of experience since the last time of updating said table.

* * * * *

UNITED STATES PATENT AND TRADEMARK OFFICE
CERTIFICATE OF CORRECTION

PATENT NO. : 4,060,716

DATED : Nov. 29, 1977

INVENTOR(S) : Paul J. Pekrul et al

Page 1 of 2

It is certified that error appears in the above-identified patent and that said Letters Patent is hereby corrected as shown below:

Column 1, line 46, "and anomalous" should read --an anomalous--.

Column 7, in the heading of the first column of the example, "CHAPTER NAME" should read --CHANNEL NAME--.

Column 10, line 53, "histoical" should read --historical--.

Column 15, the flow chart should read as shown on page 2 of this Certificate of Correction.

Signed and Sealed this

Thirty-first Day of January 1984

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,060,716

DATED : Nov. 29, 1977

INVENTOR(S) : Paul J. Pekrul et al